(12) United States Patent
Giuffre et al.

(10) Patent No.: US 6,382,207 B1
(45) Date of Patent: May 7, 2002

(54) DEVICE AND METHOD FOR PREVENTING IGNITION OF AN ENDOTRACHEAL TUBE DURING LASER SURGERY

(75) Inventors: Kenneth Giuffre, Wyckoff; Joseph Barbetta, Oradell, both of NJ (US)

(73) Assignee: Hackensack University Medical Center, Hackensack, NJ (US)

(*) Notice: Subject to any disclaimer, the term of this patent is extended or adjusted under 35 U.S.C. 154(b) by 0 days.

(21) Appl. No.: 09/732,843

(22) Filed: Dec. 8, 2000

Related U.S. Application Data (60) Provisional application No. 60/170,284, filed on Dec. 10, 1999.

(51) Int. Cl.$^7$ .................................................. A61M 9/00
(52) U.S. Cl. .......................... 128/202.24; 128/207.14; 128/207.15; 128/202.22
(58) Field of Search ................. 128/200.24, 202.24, 128/202.22, 207.14, 207.15, 908; 604/113

(56) References Cited

U.S. PATENT DOCUMENTS

| | | | | |
|---|---|---|---|---|
| 4,046,139 A | * | 9/1977 | Horn ...................... | 128/207.15 |
| 4,198,963 A | * | 4/1980 | Barkalow et al. ....... | 128/207.15 |
| 4,351,330 A | * | 9/1982 | Scarberry .............. | 128/207.15 |
| 4,383,534 A | * | 5/1983 | Peters .................... | 128/207.15 |
| 4,520,814 A | | 6/1985 | Weeks .................... | 606/2 |
| 4,601,286 A | | 7/1986 | Kaufman ................ | 128/894 |
| 4,632,108 A | | 12/1986 | Gell ....................... | 128/207.14 |
| 4,834,087 A | | 5/1989 | Coleman et al. ........ | 128/207.14 |
| 4,976,261 A | * | 12/1990 | Gluck et al. ........... | 128/207.15 |
| 4,977,904 A | | 12/1990 | Kaufman ................ | 128/856 |
| 5,014,723 A | | 5/1991 | Kaufman ................ | 128/853 |
| 5,033,479 A | | 7/1991 | Tanny .................... | 128/849 |
| 5,040,531 A | | 8/1991 | Coleman et al. ........ | 128/207.14 |
| 5,042,476 A | | 8/1991 | Smith ..................... | 128/207.14 |
| 5,065,757 A | * | 11/1991 | Dragisic et al. ........ | 128/207.15 |
| 5,311,863 A | * | 5/1994 | Toppses et al. ......... | 128/207.15 |
| 6,033,383 A | * | 3/2000 | Ginsburg ................ | 604/113 |
| 6,033,397 A | * | 3/2000 | Laufer et al. ........... | 604/113 |

\* cited by examiner

Primary Examiner—Aaron J. Lewis
(74) Attorney, Agent, or Firm—Gibbons, Del Deo, Dolan, Griffinger & Vecchione (57) ABSTRACT

A device for preventing ignition of an endotracheal tube during laser surgery is provided, wherein the device permits communication among a sensor associated with endotracheal tube and a laser which generates the laser beam. When the sensor and endotracheal tube are impinged by the laser, the sensor senses this impingement, and communicates with a controller which controls power entering the laser beam. Because of such communication, the controller impedes power entering the laser, which extinguishes the laser and prevents ignition of the endotracheal tube.

15 Claims, 3 Drawing Sheets

DEVICE AND METHOD FOR PREVENTING IGNITION OF AN ENDOTRACHEAL TUBE DURING LASER SURGERY

This application claims priority of Provisional Patent Application Ser. No. 60/170,284 filed Dec. 10, 1999.

FIELD OF THE INVENTION

The present invention relates to a device for preventing ignition of an endotracheal tube during laser surgery. More particularly, the present invention involves detection of impingement of the laser on the endotracheal tube, and communication between the endotracheal tube and the laser in order to modulate the intensity of the laser beam impinging the endotracheal tube, and prevent ignition of the endotracheal tube.

BACKGROUND OF THE INVENTION

An endotracheal tube is a tube within or passing through the trachea which opens an unobstructed airway for a patient to breathe. These tubes have numerous applications in surgical procedures, particularly in surgical procedures of the ears, nose or throat of a patient. Recently, medical advances have included the use of laser beams in surgical procedures. However, in surgical procedures of the throat, close proximity exists between the area of the patient being operated upon and the endotracheal tube. Hence, when lasers are used in such procedures, there is a real possibility of accidental impingement of the endotracheal tube with the laser beam and ignition of the endotracheal tube. Such accidental ignition can cause substantial injury to the patient. As a result, efforts have been made to minimize the potential of igniting the endotracheal tube during laser surgery.

On such effort involves providing a fire suppression and prevention assembly to the endotracheal tube, wherein the tube is surrounded by a flexible sheath that can be inflated with a non-inflammable fluid. Consequently, if the sheath is accidentally impinged with laser radiation, the airway carrying gases to the patient, e.g., oxygen, is protected and the non-inflammable fluid helps extinguish any fires before they can injure the patient. However, such a method possesses inherent limitations. In particular, the volume of the throat is extremely small. Thus, a sheath surrounding the endotracheal tube may well take up valuable space within the throat and obstruct the medical provider's view of the area of the throat upon which is being operated.

Another method for minimizing the possibility of igniting the endotracheal tube involves a device wherein the endotracheal tube is surrounded with an airtight flexible metal tube, which is resistant to laser radiation. Such a device may also comprise an upper fluid-inflatable polymeric cuff and a lower inflatable polymeric cuff, which are inflated with a fluid (liquid) that is passed through a conduit which passes through the tube, so that the upper and lower cuffs are in fluid communication. As a result, the metal tubing protects the gas being passed to the patient from the laser, and the upper cuff protects the lower cuff from the laser beam. However, this type of a device suffers from drawbacks similar to those set forth above, i.e., it takes up a large volume in the patient's throat obstructing the medical provider's view, and constrains the flexibility of the endotracheal tube.

Other methods of ameliorating the possibility of ignition of the endotracheal tube include wrapping the tube in laser beam resistant material, or in a metal foil, which reflects any stray laser radiation from the endotracheal tube. The tube can also be wrapped with a material having pores of a diameter or thickness ranging from 1/5 to 1/3 of the wavelength of a laser beam used in a laser surgical procedure. However, such methods suffer from inherent limitations. For example, they limit the flexibility of the endotracheal tube. Also, these wrappings can dislodge or unwrap from the tube during surgery, leaving the endotracheal tube exposed for possible impingement by the laser beam. Another problem with such methods, particularly the metal foil wrappings, is that laser radiation reflected from the endotracheal tube can readily strike areas of the throat, injuring the patient.

Accordingly, what is needed is a new and useful device and method for preventing ignition of an endotracheal tube, wherein the device senses the impingement of laser radiation on the endotracheal tube, and then modulates the intensity of the laser radiation, preventing ignition of the endotracheal tube.

The citation of any reference herein should not be construed as an admission that such reference is available as "Prior Art" to the instant application.

SUMMARY OF THE INVENTION

There is provided, in accordance with the present invention, a new, useful, and unobvious device for preventing ignition of an endotracheal tube during laser surgery. Such a device grants the medical provider an unobstructed view of the patient's throat and modulates the intensity of laser radiation entering the patient's throat after the laser radiation has been detected impinging the endotracheal tube.

Broadly, the present invention extends to a device for preventing ignition of an endotracheal tube during laser surgery, wherein the device comprises a sensor which is associated with the endotracheal tube, which senses impingement of a laser beam onto the endotracheal tube. A device of the invention also comprises a controller which modulates the intensity of the laser beam, wherein the controller and the sensor are in communication. When the sensor senses impingement of the laser beam on the endotracheal tube, the sensor instructs the controller to modulate the intensity of the beam impinging the endotracheal tube, which prevents ignition of the endotracheal tube. In a particular embodiment, the controller impedes the laser beam.

Numerous sensors have applications in a device of the present invention. For example, a sensor of a device of the invention can comprise a wire associated with the endotracheal tube, wherein the wire is electrically connected to a power source and a microprocessor. The microprocessor is also electrically connected to the controller. The power source can produce either direct current (DC) or alternating current (AC). When an electrical parameter of the wire, e.g, resistance, voltage, current, capacitance, impedance, etc., changes due to impingement of the laser beam onto the wire, the microprocessor measures the change in the electrical parameter, and communicates that change to the controller. The controller in turn modulates the intensity of the laser beam based upon this change in the electrical parameter.

For example, in situations where the power source is supplying direct current (DC) to the sensor, the sensor can comprise a wheatstone bridge electrically connected to a wire that is associated with the endotracheal tube, wherein the wire is also electrically connected to the power source. An electrical parameter of the wire changes when the wire is impinged with the laser beam. The association of the wire can include locating the wire on the outer surface of the tube, within the lumen of the tube, within the material that forms the tube, and/or wrapping the wire around the outer surface of the tube, wherein the wire is electrically connected to the power source. The sensor can also comprise a microprocessor that is electrically connected to the wheatstone bridge and the controller. When an electrical parameter of the wire is modulated due to impingement of the laser beam on the wire, the microprocessor measures this modulation and instructs the controller modulate the intensity of the laser beam impinging the endotracheal tube. As a result, ignition of the endotracheal tube is prevented. The electrical parameter of the wire can be voltage, resistance, current, etc. One of ordinary skill in the art can readily program the microprocessor to measure a modulation in any of these parameters using routine programming techniques.

Naturally, numerous materials can be used in a wire of a device as described above. Particular examples of such materials include, but certainly are not limited to Nichrome, a composition of 80% Ni, and 20% Cr by weight, and a resistivity of 108X $10^8$ ohm*meter.

Likewise, a large variety of lasers have applications with a device of the invention, including $CO_2$ and excimer lasers, to name only a few.

Moreover, the association of the wire with the endotracheal tube can be that the wire is on the endotracheal tube, within the material forming the endotracheal tube, or within the lumen of the endotracheal tube. In a particular embodiment of a device of the invention, wherein the wire is on the endotracheal tube, the wire is wrapped around the endotracheal tube.

The present invention further extends to a device for preventing ignition of an endotracheal tube during surgery with a laser beam generated by a laser, the device comprising:

(a) a wire associated with the endotracheal tube, wherein the wire is electrically connected to a power source, and electrical resistance of the wire increases upon impingement of the wire by the laser beam;

(b) a wheatstone bridge electrically connected to the wire;

(c) a microprocessor electrically connected to the wheatstone bridge, wherein the microprocessor measures electrical resistance of the wire; and (d) a controller which controls power entering the laser, and is electrically connected to the microprocessor, such that upon laser beam's impingement of the endotracheal tube and the wire, the microprocessor measures an increase in the electrical resistance of the wire and instructs the controller to impede power entering the laser. As a result, the laser beam is extinguished and ignition of the endotracheal tube is prevented.

Moreover, the present invention extends to a device of the present invention wherein the power source of the sensor produces alternating Current (AC) and/or radio frequency (RF). Thus, when the sensor associated with the tube is impinged by the laser beam, an electrical parameter of the sensor changes. Particular examples of AC electrical characteristics of the sensor that would change due to impingement with the laser beam include, but certainly are not limited to electrical capacitance or inductance.

Numerous sensors whose AC electrical characteristics would change due to impingement by a laser beam are well known by those of ordinary skill in the art, and are encompassed by the present invention. A particular example of such a sensor comprises:

(a) an oscillator to generate the AC frequency for sensor material excitation;

(b) an amplifier to driver to increase the power of the aforementioned AC signal;

(c) a sensing material of or associated with the endotracheal tube exhibiting a change in AC electrical characteristics of the sensing material from radiation or from heating upon impingement of the laser beam; and (d) a conditioning circuitry to amplify and isolate the measuring signal resulting from the change in AC characteristics of sensor.

The measuring signal would then be communicated to the controller, which would modulate the intensity of the laser beam impinging the endotracheal tube, and preventing ignition of the endotracheal tube.

Numerous oscillator or AC signal generation methods are readily available to the skilled artisan, and have applications in the present invention. Examples include, but certainly are not limited to operational amplifier circuits, buffer circuits, transistor circuits, and integrated circuiting combining of combinations of the aforementioned amplifier circuits, etc.

Furthermore, numerous materials whose AC electrical characteristics change due to impingement with a laser beam have applications herein. Particular examples include dielectric materials such as polyethylene or polypropylene, to name only a few.

Likewise, numerous conditioning circuitry can be used in a device of the present invention. Examples include, but certainly are not limited to analog methods such as operational amplifier circuits, buffer circuits, transistor circuits, filter circuits, mixing circuits, and integrated circuits combining of combinations of aforementioned amplifier circuits, etc. Digital devices, such as amplifiers, filters, mixers, etc. implemented on digital microcontrollers, digital signal processors, application specific integrated circuits, gate arrays, programmable logic devices, and discrete digital logical devices, to name only a few, can also be used in conditioning circuitry in a particular embodiment of a device of the present invention.

In addition, numerous controllers and methods of controller have ready applications in a device of the present invention. Particular examples include analog methods such as comparators, differentiators, integrators, and integrated circuiting combining of combinations of aforementioned amplifier circuits, to name only a few. Numerous digital methods also have applications. Particular digital methods include, but certainly are not limited to comparators, differentiators, and/or integrators implemented on digital processing elements, e.g., microprocessors, microcontrollers, digital signal processors, application specific integrated circuits, gate arrays, programmable logic devices, discrete digital logic devices, etc. These digital processing elements can be readily programmed using routine programming techniques well known to those of ordinary skill in the art.

Another sensor having applications in a device of the invention for preventing ignition of an endotracheal tube during laser surgery comprises a photocell associated with the endotracheal tube. The photocell is electrically connected to a power source. Upon impingement of the photocell by the laser beam, a voltage develops across the photocell. A microprocessor is electrically connected to the photocell and the controller. Using routine programming techniques well known to those of ordinary skill in the art, the microprocessor is programmed to measure the voltage across the photocell, and instruct the controller to modulate the intensity of the laser beam impinging the endotracheal tube. As a result, upon measuring a voltage across the photocell, the microprocessor instructs the controller to modulate the intensity of the laser beam, and prevents ignition of the endotracheal tube. Naturally, numerous photocells, including a photovoltaic cell and phototube, to name only a few, have applications herein. These photocells are further described infra. What's more, a photocell associated with an endotracheal tube can be located on the endotracheal tube, within the material forming the endotracheal tube, or within the lumen of the endotracheal tube.

What's more, the present invention further extends to a device for preventing ignition of an endotracheal tube during surger with a laser beam generated by a laser, the device comprising:

(a) a photocell associated with the endotracheal tube, wherein voltage across the photocell increases upon impingement of the photocell by the laser beam;

(b) a power source electrically connected to the photocell;

(c) a microprocessor electrically connected to the photocell, wherein the microprocessor is programmed to measure voltage across the photocell; and (d) a controller which controls power entering the laser, and is electrically connected to the microprocessor, such that upon laser beam's impingement of the endotracheal tube and the photocell, the microprocessor measures voltage across the photocell and instructs the controller to modulate the intensity of the laser beam. The photocell can be associated with the endotracheal tube such that the photocell is on the endotracheal tube, within the material forming the endotracheal tube, or within the lumen of the endotracheal tube.

Naturally, numerous types of controllers, well known and readily available to the skilled artisan, have applications in a device of the invention as set forth above.

In addition, the present invention extends to a device for preventing ignition of an endotracheal tube during surgery with a laser beam generated by a laser, the device comprising:

(a) a photocell on the endotracheal tube, wherein the photocell is electrically connected to a power supply, wherein voltage across the photocell increases upon impingement of the photocell by the laser beam;

(b) a microprocessor electrically connected to the photocell wherein the microprocessor measures voltage across the photocell, and a predetermined voltage is programmed into the microprocessor; and (c) a switch which controls power entering the laser, wherein the switch is electrically connected to the microprocessor, such that upon laser beam's impingement of the endotracheal tube and the photocell, the microprocessor measures voltage across the photocell and instructs the switch to impede power entering the laser when voltage measured across the photocell is greater than the predetermined voltage.

Naturally, numerous switches and methods of modulating the intensity of the laser beam in a device of the present invention have applications herein. Particular examples include, but certainly are not limited to delivery system modulators, connections to laser manufacturer equipment, and cutoffs for laser power, to name only a few.

Furthermore, a wide variety of methods for implementing a switch in a device of the present invention are available to a skilled artisan, and are encompassed by the present invention. In particular, a switch for modulating the intensity of the laser beam can comprise a mirror or surface that is reflective to the wavelength of the laser beam. An actuator, under the control of the controller of a device of the invention, would position the reflector to deflect the laser from the endotracheal tube, upon the controller's determination that the laser beam is impinging the endotracheal tube. The reflector can be operated to deflect the laser beam onto an energy absorption material to safely absorb the laser energy. This absorption material would be associated with or connected to an energy dissipater to safely dissipate the energy of the laser beam to surrounding air. A connection to laser manufacturer equipment can comprise an output of the controller, such as a relay, transistor, digital signal, etc. When the controller determined, based upon input from the sensor, that the laser beam is impinging the endotracheal tube, output of the controller would cause the laser equipment to modulate the intensity of the laser beam. A cutoff for the laser power, which also can serve as a controller in a device of the present invention, can comprise a device controlled by the controller, wherein the cutoff modulates power to the laser equipment upon the controller's determination of impingement of the laser beam can comprise activated by the controller. As a result, the intensity of the laser beam is modulated, and ignition of the endotracheal tube is prevented. Examples of such a device include relays, contractors, and/or transistors, to name only a few.

Optionally, the present invention can further extend to an alarm, which is visual, audible, vibrational, or a combination thereof, which alerts the medical professional that laser impingement upon the endotracheal tube has occurred. Numerous types of alarms well known to those of ordinary skill in the art can readily be incorporated into a device of the invention using routine engineering techniques.

Furthermore, the present invention extends to methods for preventing ignition of an endotracheal tube during laser surgery. Broadly, a method of the present comprises providing a sensor which can sense impingement of a laser beam; associating the sensor with the endotracheal tube, which senses impingement of a laser beam onto the endotracheal tube; and providing a controller which modulates the intensity of the laser beam, wherein the controller and the sensor are in communication. When the sensor senses impingement of the laser beam on the endotracheal tube, the sensor instructs the controller to modulate the intensity of the beam, which prevents ignition of the endotracheal tube. In a particular embodiment, the controller impedes the laser beam.

Numerous examples of sensors, controllers, power sources, etc. which have applications in a method of the invention are described above.

Accordingly, it is an object of the present invention to provide real-time information to a medical provider performing laser surgery regarding the impingement of the laser beam upon an endotracheal tube within the patient. As a result, the medical provide can extinguish the beam prior to igniting the endotracheal tube.

It is another object of the present invention to provide a feedback mechanism and communication between the laser and the endotracheal tube, such that upon impingement of the laser beam on the endotracheal tube, the intensity of the laser beam is modulated, and ignition of the endotracheal tube is prevented.

These and other objects of the present invention will be better appreciated by reference to the following drawings and Detailed Description.

DETAILED DESCRIPTION OF THE INVENTION

The present invention involves communication between a sensor associated with the endotracheal tube and the laser such that when the impingement of the laser beam is detected upon an endotracheal tube during a laser surgical procedure, the sensor instructs the controller to modulate the intensity of the laser beam, preventing the ignition of the endotracheal tube. Consequently, an apparatus of the invention is new, useful and nonobvious in light of heretofore known devices, which are principally concerned with protecting the endotracheal tube from laser radiation, and provide no communication between the endotracheal tube via a sensor, and the laser.

Accordingly, the present invention extends to a device for preventing ignition of an endotracheal tube during laser surgery, wherein the device comprises a sensor which is associated with the endotracheal tube and can sense impingement of the laser beam, and a controller which is electrically connected to the sensor. When the sensor detects impingement of the laser beam upon the endotracheal tube, it instructs the controller to modulate the intensity of the laser beam impinging the endotracheal tube. This modulation prevents ignition of the endotracheal tube.

Moreover, numerous words and phrases used throughout the instant Specification and Claims are defined below:

As used herein, the terms "modulation" and "modulate" refer to the adjustment of adaptation of the intensity of the laser beam impinging the endotracheal tube such that the intensity is decreased. In a particular embodiment, modulation refers to decreasing the intensity of the laser beam to zero.

As used herein, the term "intensity" refers to the amount of degree of strength of light per unit area or volume.

As used herein, the phrase "endotracheal tube" refers to a tube within or passing through the trachea which opens an unobstructed airway for a patient to breath, and has a lumen which permits gas, such as oxygen, to be passed to the patient, particularly during a surgical procedure. An endotracheal tube can be made of numerous materials, including, but not limited to polypropylene, polyethylene, polytrimethylpentene, polytetrafluoroethylene, polyvinylidene difluroide, polysulfone, polydimethylsiloxane (silicone rubber), nitrile rubber, neoprene rubber, silicone-polycarbonate copolymers, fluoroelastomers, polyurethane, polyvinyl chloride, polybutadiene, polyolefin elastomers, polyesters, or polyethers.

As used herein, the term "ignition" refers to the raising of the temperature of an endotracheal tube to the minimum temperature at which it will continue to burn without external heat.

As used herein, the term "associated" with respect to a sensor and an endotracheal tube refers to the sensor and the endotracheal tube being connected, joined together, or combined. Thus, a sensor associated with an endotracheal tube can be on the endotracheal tube, within the endotracheal tube, i.e., imbedded within the endotracheal tube, or in the lumen of the endotracheal tube.

As used herein, the phrase "electrical resistance" refers to the opposition of a body or substance to a current passing through it, dissipating electrical energy. Generally, resistance is measured in Ohms ($\Omega$).

As used herein, the phrase "wheatstone bridge" refers to an electrical circuit used to determine an unknown electrical resistance by adjusting a known resistance so that the measured current within the circuit is zero. A more detailed description of a wheatstone bridge is set forth infra.

As used herein, the term "microprocessor" refers to an integrated circuit that contains the entire central processing unit of a computer on a single chip, and can programmed to perform functions.

As used herein, the term "impede" in regards to a controller refers to the controller retarding or obstructing power entering the laser.

As used herein, the term "voltage" (E) refers to an electromotive force or potential difference, generally measured in Volts (V).

As used herein, the phrase "photocell" refers to an electronic device having an electrical output that varies in response to incident radiation, such as a laser beam. Particular examples of photocells having applications herein include, but certainly are not limited to photovoltaic cells, phototubes, and photomultipliers, to name only a few, which are described infra.

As used herein, the singular forms "a", "an" and "the" include plural referents unless the context clearly dictates otherwise.

As used herein the term "laser" refers to any of several devices that convert incident electromagnetic radiation of mixed frequencies to one or more discrete frequencies of highly amplified and coherent ultraviolet, visible, or infrared radiation.

As used herein, the phrase "laser beam" refers to a concentrated stream of electromagnetic radiation produced by a laser.

As used herein, the phrase "electrically connected" regarding elements of a device of the invention refers to a connection between the elements that permits an electric current to pass from one element to the other element.

As explained above, the present invention extends to a device for preventing ignition of an endotracheal tube during laser surgery, wherein the device comprises a sensor which is associated with the endotracheal tube, which senses impingement of a laser beam onto the endotracheal tube. A device of the invention also comprises a controller which modulates the intensity of the laser beam impinging the endotracheal tube, wherein the controller and the sensor are in communication. When the sensor senses impingement of the laser beam on the endotracheal tube, the sensor instructs the controller to modulate the intensity of the beam, which prevents ignition of the endotracheal tube. In a particular embodiment, the controller impedes the laser beam.

What's more, the present invention further extends to a method for preventing ignition of an endotracheal tube during laser surgery, comprising the steps of providing a sensor which can sense impingement of a laser beam; associating the sensor with the endotracheal tube, which senses impingement of a laser beam onto the endotracheal tube; and providing a controller which modulates the intensity of the laser beam, wherein the controller and the sensor are in communication. When the sensor senses impingement of the laser beam on the endotracheal tube, the sensor instructs the controller to modulate the intensity of the beam, which prevents ignition of the endotracheal tube. In a particular embodiment, the controller impedes the laser beam.

As explained above, FIG. 1 is a schematical view of an embodiment of a device of the invention, wherein endotracheal tube (1) is inserted into trachea (2) of a patient. An endotracheal tube which can be used with a device of the invention has an inner lumen (not shown) through which gas, such as oxygen, is passed to the patient during surgery. Thus, the inner lumen of endotracheal tube (1) is in fluid communication with an intubation or anesthetizing apparatus (not shown). Endotracheal tube (1) can be made of any biocompatible, pharmaceutically inert material. Particular examples of such materials include, but certainly are not limited to polypropylene, polyethylene, polytrimethylpentene, polytetrafluoroethylene, polyvinylidene difluoride, polysulfone, polydimethylsiloxane (silicone rubber), nitrile rubber, neoprene rubber, silicone-polycarbonate copolymers, fluoroelastomers, polyurethane, polyvinyl chloride, polybutadiene, polyolefin elastomers, polyesters, or polyethers.

Referring again to FIG. 1, sensor (3) is associated with endotracheal tube (1). In a device of the present invention, sensor (3) associated with endotracheal tube (1) can be on endotracheal tube (1), embedded within the material forming endotracheal tube (1), or within the lumen (not shown) of endotracheal tube (1). Particular examples of sensors having applications herein are described infra.

Figure 1:
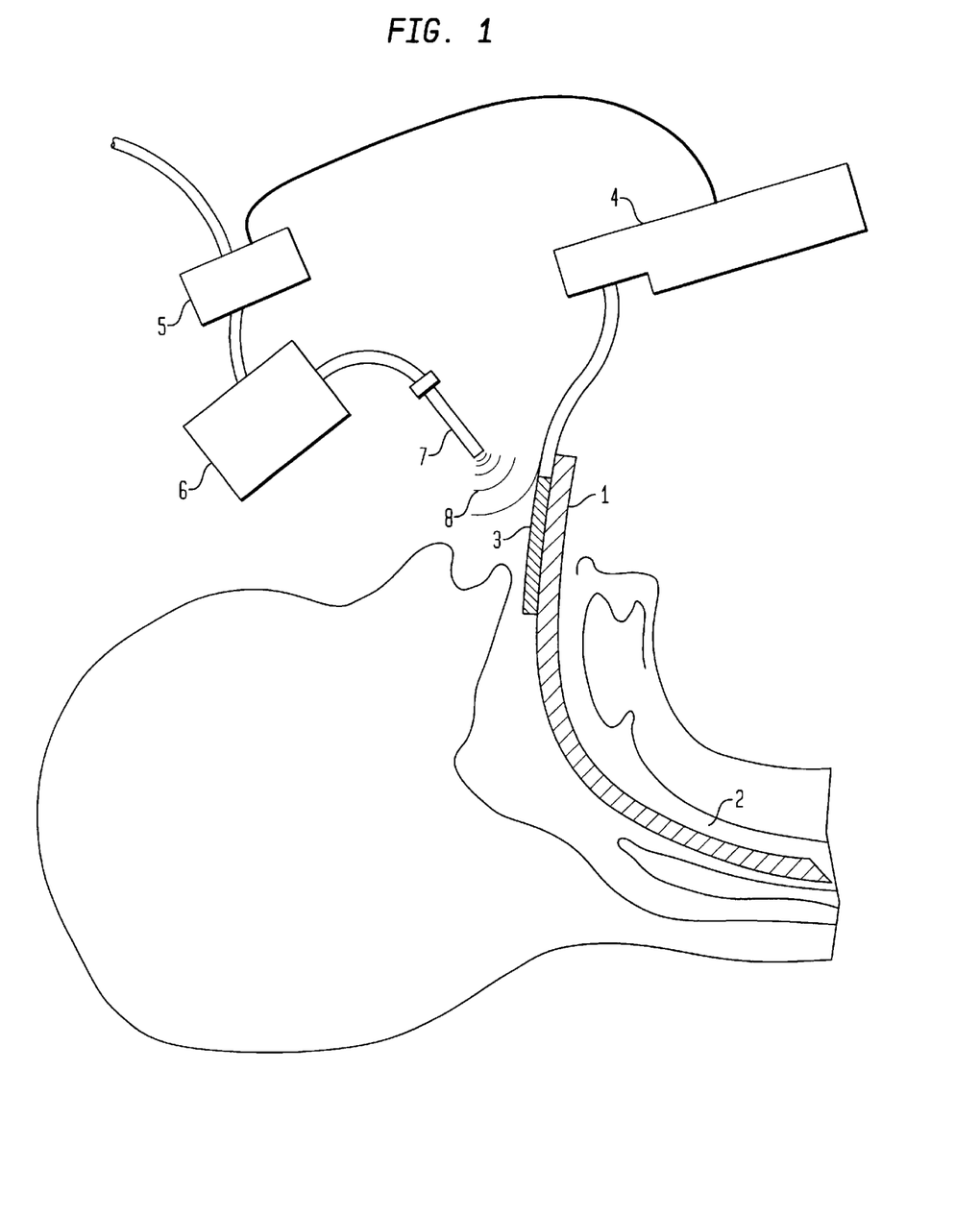
FIG. 1 is a schematical view of an embodiment of a device of the Invention.

Still referring to FIG. 1, sensor (3) is electrically connected to microprocessor (4), which in turn is electrically connected to controller (5). A power source (not shown) is electrically connected to sensor (3). The power source can provide either direct current or alternating current. Numerous microprocessors that are readily commercially available to a skilled artisan that can programmed using routine programming techniques have ready applications in a device or method of the present Invention. Microprocessor (4) can measure a change in an electrical parameter of the sensor, and thus quantify any impingement of a laser beam upon sensor (3) and endotracheal tube (1). Particular examples of such parameters are described above, and include resistance, current, voltage, impedance, capacitance, etc. Thus, microprocessor (4) can be readily programmed to recognize a predetermined or threshold value of the parameter being measured regarding sensor (3), which is related to the impingement of laser beam (8) on sensor (3) and endotracheal tube (1).

Microprocessor (4) is electrically connected to controller (5), which in turn is electrically connected to laser (6). In the embodiment of a device of the present invention schematically shown in FIG. 1, controller (5) is electrically upstream from laser (6) and electrically downstream from a power supply (not shown). Thus, as explained infra, the controller operates to impeding power entering the laser. However, numerous controllers, including deflectors as described above, have readily applications in a device of the present invention.

A wave guide (7) permits the movement of laser (6) and thus the aiming and focusing of laser beam (8) on a particular target within the patient. Thus, in an embodiment of a device of the present invention as schematically set forth in FIG. 1, should laser beam (8) impinge sensor (3), and endotracheal tube (1) during a laser surgical procedure, microprocessor (4) can measure a change in a particular parameter of sensor (l), e.g., resistance, current, voltage, capacitance, etc., which reflects the impingement. Microprocessor (4) can then compare the value of the measured parameter with a threshold or predetermined value programmed into microprocessor (4). Based upon this comparison, microprocessor (4) may instruct controller (5) to impede power produced by the power source (not shown) from entering laser (6). As a result, laser beam (8) generated to laser (6), and directed by laser (7) is extinguished, preventing further impingement of laser beam (8) upon endotracheal tube (1), and ignition of endotracheal tube (1).

As explained above, numerous sensors have applications herein. One type of sensor having applications herein comprises a wire associated with endotracheal tube (1), wherein the electrical resistance of the wire, an electrical parameter, increases upon impingement of the wire by laser beam (8). Numerous types of wires have applications in such an embodiment of a device of the present invention, including, but certainly not limited to nichrome, which is described above. Moreover, the association of the wire with the endotracheal tube can be as described above, including wrapping the wire around the endotracheal tube.

What's more, numerous means are readily available to the skilled artisan for measuring an increase in the electrical resistance of the wire. A wheatstone bridge is an example of one such means, and is very advantageous for the measure of parameters such as resistance, inductance, and capacitance. A schematically view of a typical wheatstone bridge is set forth in FIG. 2, and a schematically view of the circuit of a wheatstone bridge is set forth in FIG. 3. Broadly, a wheatstone bridge comprises electrical resistors (9), (10), (11), and (12) arranged in a diamond orientation. The values of the electrical resistance of resistors (9), (10) and (11) are known, while the electrical resistance of resistor (12) is unknown. In a particular embodiment of a device of the present invention, resistor (12) is the wire described above which is associated with the endotracheal tube.

Another nonlimiting example of a sensor having applications in a device of the present invention, wherein the power source electrically connected to the sensor provides AC power, comprises:

(a) an oscillator to generate the AC frequency for sensor material excitation;

(b) an amplifier to driver to increase the power of the aforementioned AC signal;

(c) a sensing material of or associated with the endotracheal tube exhibiting a change in AC electrical characteristics of the sensing material from radiation or from heating upon impingement of the laser beam; and (d) a conditioning circuitry to amplify and isolate the measuring signal resulting from the change in AC characteristics of sensor.

The measuring signal would then be communicated to the controller, which would modulate the intensity of the laser beam, and prevent ignition of the endotracheal tube.

Numerous oscillator or AC signal generation methods are readily available to the skilled artisan, and have applications in the present invention. Examples include, but certainly are not limited to operational amplifier circuits, buffer circuits, transistor circuits, and integrated circuiting combining of combinations of the aforementioned amplifier circuits, etc.

Furthermore, numerous materials whose AC electrical characteristics change due to impingement with a laser beam have applications herein. Particular examples include dielectric materials such as polyethylene or polypropylene, to name only a few.

Likewise, numerous conditioning circuitry can be used in a device of the present invention. Examples include, but certainly are not limited to analog methods such as operational amplifier circuits, buffer circuits, transistor circuits, filter circuits, mixing circuits, and integrated circuits combining of combinations of aforementioned amplifier circuits, etc. Digital devices, such as amplifiers, filters, mixers, etc. implemented on digital microcontrollers, digital signal processors, application specific integrated circuits, gate arrays, programmable logic devices, and discrete digital logical devices, to name only a few, can also be used in conditioning circuitry in a particular embodiment of a device of the present invention.

Figure 2:
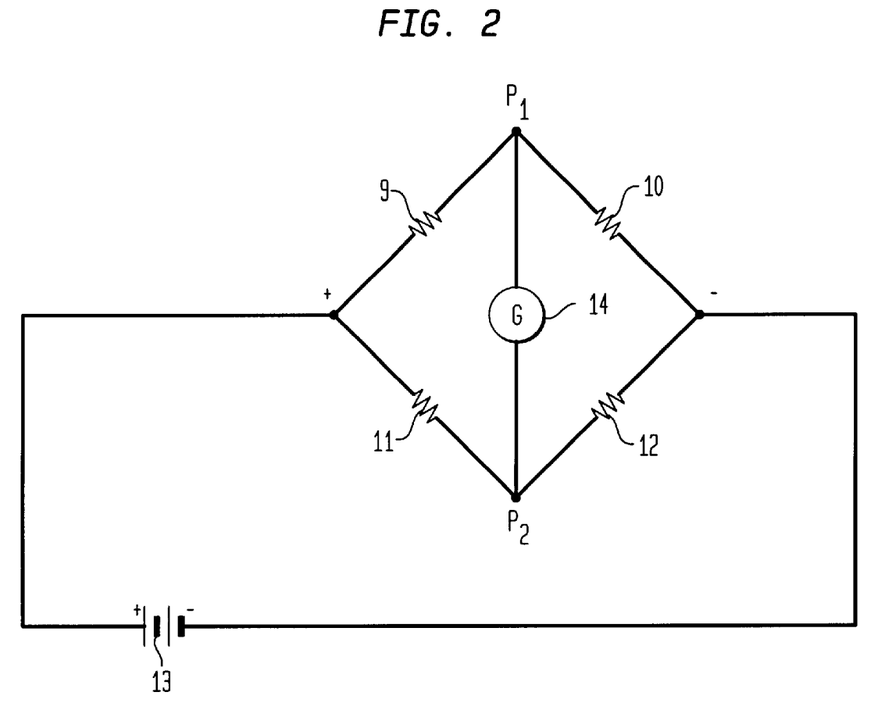
FIG. 2 is a schematical view of a wheatstone Bridge.
Figure 3:
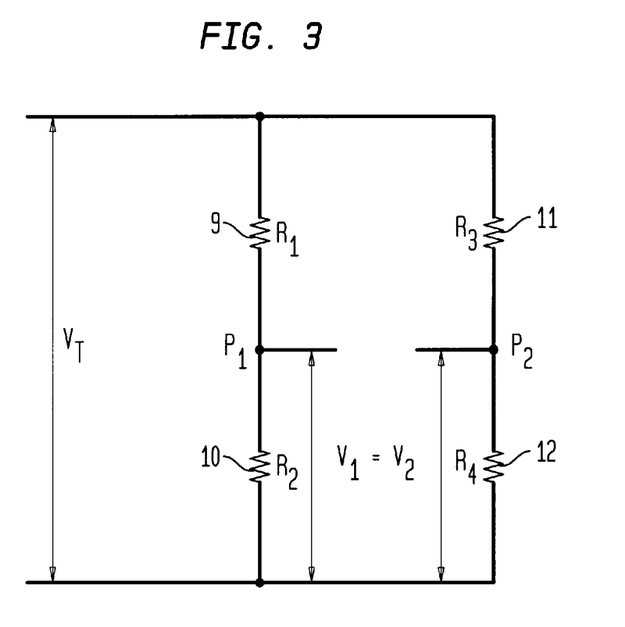
FIG. 3 is a schematical view of the electrical circuit of a wheatstone bridge.

Referring to FIG. 2, an excitation voltage, produced by power supply (13), is applied between the points $P_3$ and $P_4$ of the diamond. Power supply (13) may be either an alternating current (AC) or direct current (DC) power supply. The voltage across $P_1$ and $P_2$ is measured with voltmeter (14). The resistance of resistor $R_2$ is then adjusted until no voltage is measured across the points $P_1$ and $P_2$, and the bridge is deemed "balanced". Consequently, under conditions when the bridge is balanced, the electrical potential of the wire of the sensor ($E_w$) equals the voltage drop across resistor (10) ($E_2$), and the voltage drop across resistor (9) ($E_1$) equals the voltage drop across resistor (9) ($E_3$). For example, FIG. 3 depicts the circuit of a balanced wheatstone bridge, wherein $V_1=V_2$.

Ohm's law states that the current 1 (in amperes (A)) flowing in a conductor is directly proportional to the applied voltage E (in volts) and inversely proportional to the resistance R (in ohms Ω) of the conductor. Thus:

$$i=E/R, \text{ or } R=E/i \qquad (1)$$

As explained above, in a Wheatstone bridge, $$E_w=E_{10} \text{ and } E_9=E_{11} \qquad (2)$$

Thus, substituting Ohm's law into equations of (2):

$$i_w R_w = i_{10} R_{10} \text{ and } i_9 R_9 = i_{11} R_{11} \qquad (3)$$

and $$[(R_w i_w)/(R_{11} i_{11})] = [(R_{10} i_{10})/(R_9 i_9)] \qquad (4)$$

Since the current passing through resistors $R_1$ and $R_2$ is the same, and the current passing through $R_3$ and the wire are the same, the currents cancel and Equation (4) and can be solved for $R_w$:

$$R_w = [(R_{10} R_{11})/R_9]. \qquad (5)$$

It is well within the routine skills of a skilled artisan to program a microprocessor to calculate $R_w$ using the equations described above. Moreover, a microprocessor can be readily programmed using routine programming procedures to recognize a predetermined electrical resistance for the wire, and compare the predetermined electrical resistance to the electrical resistance measured in the wire. Since the electrical resistance of the wire increases when impinged by the laser beam, this increase will be readily determined by the microprocessor, and compared to the predetermined electrical resistance. If the measured resistance is greater than or equal to the predetermined electrical resistance, the microprocessor will instruct the controller to impede power entering the laser, thus, extinguishing the laser beam and, preventing the ignition of the endotracheal tube.

Another sensor having applications in a device of the invention is a photocell, which employs the photoelectric effect in its operation. The photoelectric effect is the ejection of electrons from a surface of a metal or other material when impinged by electromagnetic radiation, i.e., laser light, wherein the frequency of the electromagnetic radiation exceeds a threshold value characteristic of the particular metal or material.

Figure 4:
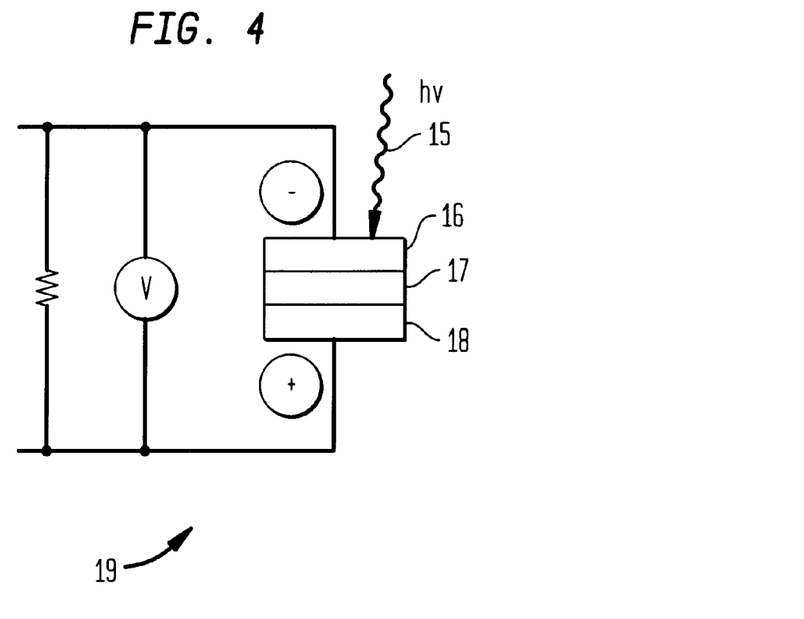
FIG. 4 is a schematical view of a photovoltaic cell.

An example of a photocell having applications herein is a photovoltaic cell, schematically set forth in FIG. 4. A photovoltaic cell (19) measures the intensity of photons impinging the cell by means of the voltage developed across semiconductor layer (17). In particular, a laser beam (hv) (15) traverses semitransparent layer (16) and impinges semiconductor layer (17). The impingement of laser beam (15) upon semiconductor layer (17) causes the expulsion of electrons from layer (17). These electrons are collected on collection layer (18), thus producing a voltage across the photovoltaic cell. In a particular example, wherein laser beam (15) is from a $CO_2$ laser, semiconductor layer (17) is formed of silicon and/or gallium Likewise, if the laser beam (15) is an excimer laser, semiconductor layer (10) is formed of gallium/arsenide. Likewise, semi-transparent layer (16) and collection layer (18) can be made of numerous materials, including silver. In addition, the photovoltaic cell can be associated with an endotracheal tube such that the cell is on the tube, within the material forming the tube, or within the lumen of the tube. What's more, a plurality of photovoltaic cells can be associated with the tube throughout the entire length of the tube, wherein each cell is electrically connected to the microprocessor.

The voltage that results across photovoltaic cell (19) is dependent upon the number of photons of the laser beam that strike semiconductor layer (17). Furthermore, the voltage across the photovoltaic cell can readily be measured and supplied to the microprocessor (not shown) for analysis, e.g., for comparison to the predetermined voltage programmed into the microprocessor. Hence, when the voltage measured across photovoltaic cell (19) is greater than or equal to the predetermined voltage, the microprocessor (not shown) will instruct the controller to impede power entering the laser (not shown), which discontinues laser beam (15) and prevents ignition of the endotracheal tube.

Figure 5:
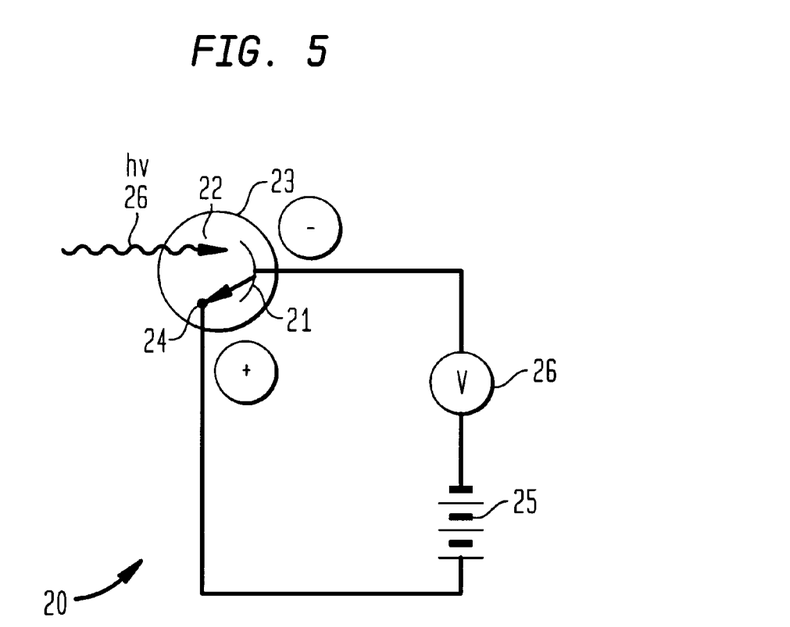
FIG. 5 is a schematical view of a phototube

Another example of a photocell having applications in a device of the present invention is a phototube (20), which is schematically shown in FIG. 5. A photoelectric surface (21) is negatively charged, e.g. a cathode, and contained within chamber (22) formed by transparent envelope (23). Chamber (22) is evacuated forming a vacuum therein. Anode (24) is also within chamber (23). Photoelectric surface (21) and anode (24) are electrically connected via power supply (25). When photons of laser beam (26) impinge photoelectric surface (21), electrons are dislodged from surface (21) and migrate to anode (24). As a result, a current flows through the tube, which can be measured with voltmeter (26). Voltmeter (26) is electrically connected to a microprocessor (not shown), which compares the measured voltage in the phototube with a predetermined voltage programmed into the microprocessor. If the measured voltage is greater than or equal to the predetermined voltage, the microprocessor instructs the controller to impede power entering the laser, extinguishing laser beam (26) and preventing ignition of the endotracheal tube. Naturally, according to Ohm's law stated above, once two of the variables are known, the remaining can readily be determined.

Numerous materials can be used to form photoelectric surface (21). Particular examples of such materials are set forth above, and includes, but certainly is not limited to a metal base comprising a first layer of semiconductor deposited on top of the metal layer, and a second layer of semitransparent silver deposited on top of the semiconductor level. Another example of such a material comprises cesium deposited upon an electrode. In a particular embodiment, photoelectric surface (21) is a cesium-coated photocathode. Furthermore, any electrically conducting material, such as copper, silver, gold, or electrically conducting polymer, to name only a few, can serve as anode (24).

In an embodiment of a device of the invention wherein the sensor is a phototube, the phototube is associated the endotracheal tube as such that the phototube is on the endotracheal tube, the phototube is within the material forming the endotracheal tube, or the phototube is within the lumen of the endotracheal tube. In addition, a device of the invention can employ a plurality of phototubes associated with the endotracheal tube, wherein the phototubes are spatially arranged along the length of the endotracheal tube. Each phototube is electrically connected to the microprocessor.

What's more, the sensor in an embodiment of the invention can comprise an optical fiber that is wrapped around the endotracheal tube, wherein the end of the optical fiber is connected to a photocell. When a photon from the laser beam impinges the endotracheal tube, it can pass into the optical fiber, and be propagated to the photocell. There, a change in voltage across the photocell can be measured, thus indicating the endotracheal tube has been impinged with the laser beam.

Many other variations and modifications of a device of the invention will apparent to those skilled in the art without departing from the spirit and scope of the invention. The above-described embodiments are therefore, included to be merely exemplary, and all such variations and modifications are intended to be included within the scope of the invention as defined in the appended Claims.

What is claimed is:

1. A device for preventing ignition of an endotracheal tube during surgery with a laser beam generated by a laser, said device comprising:
    (a) a sensor which can sense impingement of said laser beam, wherein said sensor is operatively connected to said endotracheal tube; and
    (b) a controller which modulates the intensity of said beam, wherein said controller and said sensor are in communication;
    such that upon sensing impingement of said laser beam on said endotracheal tube, said sensor instructs said controller to modulate the intensity of said laser beam impinging said endotracheal tube, and prevent ignition of said endotracheal tube.

2. The device of claim 1, wherein said sensor comprises:
    (a) a wire associated with said endotracheal tube, wherein said wherein said wire is electrically connected to a power source, and an electrical parameter of the wire changes upon impingement by said laser beam; and
    (b) a microprocessor electrically connected to said wire and said controller;
    wherein said microprocessor measures the change in said electrical parameter of said wire, and instructs said controller to modulate the intensity of said beam impinging said endotracheal tube based upon the change in the electrical parameter.

3. The device of claim 2, wherein said microprocessor instructs said controller to impede power entering said laser.

4. The device of claim 2, wherein said electrical parameter comprises voltage, resistance, capacitance, current, or impedance of said wire.

5. The device of claim 2, wherein said wire is on said endotracheal tube.

6. The device of claim 5, wherein said wire is wrapped around endotracheal tube.

7. The device of claim 2, wherein said wire is within said endotracheal tube.

8. The device of claim 1, wherein said sensor electrically connected to an alternating current power source, and said sensor comprises:
    (a) an oscillator to generate the AC frequency for sensor material excitation;
    (b) an amplifier to driver to increase the power of the aforementioned AC signal;
    (c) a sensing material associated with the endotracheal tube exhibiting a change in AC electrical characteristics of the sensing material from radiation or from heating upon impingement of the laser beam; and
    (d) a conditioning circuitry to amplify and isolate the measuring signal resulting from the change in AC characteristics of sensor.

9. The device of claim 1, wherein said sensor comprises
    (a) a photocell associated with said endotracheal tube, wherein said photocell is electrically connected to a power source, and voltage across said photocell changes due to impingement of said photocell by said laser beam; and
    (b) a microprocessor electrically connected to said photocell and said controller;
    wherein said microprocessor measures voltage across said photocell, and instructs said controller to modulate intensity of said laser beam impinging said endotracheal tube upon an increase of voltage across said photocell.

10. The device of claim 9, wherein said microprocessor instructs said controller to impede power entering said laser when voltage measured across said photocell is greater than a predetermined voltage programmed into said microprocessor.

11. The device of claim 9, wherein said photocell is on said endotracheal tube.

12. The device of claim 9, wherein said photocell is within said endotracheal tube.

13. A device for preventing ignition of an endotracheal tube during surgery with a laser beam generated by a laser generator, said device comprising:
    (a) a wire operatively connected to said endotracheal tube, wherein said wire is electrically connected to a power source, and electrical resistance of said wire increases upon impingement of said wire by said laser beam;
    (b) a wheatstone bridge electrically connected to said wire;
    (c) a microprocessor electrically connected to said wheatstone bridge, wherein said microprocessor measures electrical resistance of said wire;
    (d) a controller which controls power entering said laser generator, and is electrically connected to said microprocessor;
    such that upon laser beam's impingement of said endotracheal tube and said wire, said microprocessor measures the change in electrical resistance of said wire due to impingement by said laser beam, and instructs said controller to modulate the intensity of said laser beam, preventing ignition of said endotracheal tube.

14. The device of claim 13, wherein said microprocessor instructs said switch to impede power entering said generator when said electrical resistance of said wire is greater than a predetermined resistance programmed into said microprocessor.

15. A method for preventing ignition of an endotracheal tube in a patient during laser surgery on the patient, the method comprising the steps of:

providing a sensor which can sense impingement of a laser beam;

operatively connecting the sensor with the endotracheal tube, which senses impingement of a laser beam onto the endotracheal tube; and providing a controller which modulates the intensity of the laser beam, wherein the controller and the sensor are in communication;

such that when the sensor senses impingement of the laser beam on the endotracheal tube, the sensor instructs the controller to modulate the intensity of the beam, which prevents ignition of the endotracheal tube.

* * * * *